US009289247B2

(12) United States Patent
Arthur et al.

(10) Patent No.: US 9,289,247 B2
(45) Date of Patent: Mar. 22, 2016

(54) SURGICAL TOOL HOLDER

(71) Applicant: KYPHON SARL, Neuchatel (CH)

(72) Inventors: Amy L. Arthur, Mountain View, CA (US); Mojan Goshayeshgar, Atherton, CA (US); Michael A. Smith, San Jose, CA (US); William Porter McRoberts, Fort Lauderdale, FL (US); Neil S. Sasaki, San Jose, CA (US)

(73) Assignee: KYPHON SÀRL, Neuchâtel (CH)

( * ) Notice: Subject to any disclaimer, the term of this patent is extended or adjusted under 35 U.S.C. 154(b) by 105 days.

(21) Appl. No.: 13/832,834

(22) Filed: Mar. 15, 2013

(65) Prior Publication Data

US 2014/0277199 A1 Sep. 18, 2014

(51) Int. Cl.
*A61B 17/70* (2006.01)
*A61B 17/90* (2006.01)
*A61B 19/02* (2006.01)
*A61B 19/00* (2006.01)

(52) U.S. Cl.
CPC ......... *A61B 17/7074* (2013.01); *A61B 19/0256* (2013.01); *A61B 19/201* (2013.01); *A61B 19/26* (2013.01)

(58) Field of Classification Search
CPC ...................... A61B 17/7074; A61B 2017/3405–2017/3411; A61B 2017/348–2017/3492; A61B 2017/347; A61B 19/201
USPC .......................... 606/86 A, 96, 130
See application file for complete search history.

(56) References Cited

U.S. PATENT DOCUMENTS

| 3,457,922 | A  | * | 7/1969  | Ray ................................ 606/130 |
| 4,593,681 | A  | * | 6/1986  | Soni ............................... 600/102 |
| 4,805,615 | A  | * | 2/1989  | Carol ............................. 606/130 |
| 4,809,694 | A  | * | 3/1989  | Ferrara .......................... 606/130 |
| 4,955,891 | A  | * | 9/1990  | Carol ............................. 606/130 |
| 5,279,575 | A  | * | 1/1994  | Sugarbaker .................... 604/174 |
| 5,375,588 | A  | * | 12/1994 | Yoon ............................. 600/114 |
| 5,540,648 | A  | * | 7/1996  | Yoon ............................. 600/114 |
| 5,569,290 | A  | * | 10/1996 | McAfee ......................... 606/185 |
| 5,658,272 | A  | * | 8/1997  | Hasson ............................. 606/1 |
| 5,810,712 | A  |   | 9/1998  | Dunn |
| 6,327,491 | B1 | * | 12/2001 | Franklin et al. ............... 600/429 |
| 6,488,620 | B1 | * | 12/2002 | Segermark et al. ........... 600/208 |
| 6,491,699 | B1 | * | 12/2002 | Henderson et al. ............ 606/130 |
| 6,582,420 | B2 | * | 6/2003  | Castaneda et al. ................ 606/1 |
| 6,663,597 | B1 |   | 12/2003 | Windheuser et al. |
| 6,902,569 | B2 |   | 6/2005  | Parmer et al. |
| 7,241,298 | B2 | * | 7/2007  | Nemec et al. ................ 606/86 R |
| 7,343,635 | B2 | * | 3/2008  | Jackson ............................ 5/611 |
| 7,637,915 | B2 | * | 12/2009 | Parmer et al. ................. 606/108 |
| 7,699,854 | B2 | * | 4/2010  | Mazzocchi et al. ........... 606/130 |
| 7,753,901 | B2 |   | 7/2010  | Piskun et al. |
| 8,192,445 | B2 | * | 6/2012  | Parmer et al. ................. 606/130 |
| 8,343,047 | B2 | * | 1/2013  | Albrecht et al. .............. 600/206 |
| 8,460,002 | B2 | * | 6/2013  | Wang et al. .................... 434/262 |
| 8,622,970 | B2 | * | 1/2014  | Wingardner et al. ..... 604/164.09 |
| 8,771,290 | B2 | * | 7/2014  | Mitchell et al. ............... 606/130 |
| 8,845,655 | B2 | * | 9/2014  | Henderson et al. ........... 606/130 |
| 8,979,847 | B2 | * | 3/2015  | Belcher et al. .................. 606/79 |

(Continued)

*Primary Examiner* — Jacqueline Johanas

(74) *Attorney, Agent, or Firm* — Martin & Ferraro LLP

(57) ABSTRACT

A surgical tool holder includes a flange comprising a body defining a first surface and a second surface, a first end and second end. The second surface defines a first opening configured for disposal of a cannula, wherein the first end of the flange is configured to engage at least a portion of skin of a patient to prevent the cannula from moving into the patient.

10 Claims, 7 Drawing Sheets

(56) References Cited

U.S. PATENT DOCUMENTS

| | | | |
|---|---|---|---|
| 2003/0040753 A1* | 2/2003 | Daum et al. | 606/96 |
| 2004/0039396 A1* | 2/2004 | Couture et al. | 606/87 |
| 2004/0267284 A1* | 12/2004 | Parmer et al. | 606/130 |
| 2006/0085010 A1* | 4/2006 | Lieberman | 606/99 |
| 2006/0192319 A1* | 8/2006 | Solar | 264/271.1 |
| 2008/0183191 A1* | 7/2008 | Schoepp | 606/130 |
| 2008/0228195 A1* | 9/2008 | von Jako et al. | 606/130 |
| 2009/0142739 A1* | 6/2009 | Wang et al. | 434/262 |
| 2010/0030232 A1* | 2/2010 | Zehavi et al. | 606/130 |
| 2010/0114110 A1* | 5/2010 | Taft et al. | 606/108 |
| 2010/0204714 A1* | 8/2010 | Shoham | 606/130 |
| 2011/0166573 A1* | 7/2011 | Wenk et al. | 606/71 |
| 2012/0310246 A1* | 12/2012 | Belcher et al. | 606/80 |
| 2013/0184707 A1* | 7/2013 | Mirza et al. | 606/59 |
| 2013/0190809 A1* | 7/2013 | Vidlund et al. | 606/213 |
| 2014/0018822 A1* | 1/2014 | Main | 606/130 |
| 2014/0257418 A1* | 9/2014 | Arthur | 606/86 R |
| 2014/0257419 A1* | 9/2014 | Arthur et al. | 606/86 R |
| 2014/0276561 A1* | 9/2014 | Arthur et al. | 604/506 |
| 2014/0276875 A1* | 9/2014 | Arthur et al. | 606/93 |
| 2014/0276876 A1* | 9/2014 | Arthur et al. | 606/93 |
| 2014/0277199 A1* | 9/2014 | Arthur et al. | 606/86 A |
| 2014/0277209 A1* | 9/2014 | Arthur et al. | 606/86 R |
| 2014/0277210 A1* | 9/2014 | Arthur et al. | 606/86 R |
| 2014/0288578 A1* | 9/2014 | Solar et al. | 606/130 |

* cited by examiner

SURGICAL TOOL HOLDER

TECHNICAL FIELD

The present disclosure relates to a surgical tool holder configured for use in the treatment of bone defects, such as, for example, bone fractures.

BACKGROUND

Lumbar spinal stenosis (LSS) may occur from hypertrophied bone or ligamentum flavum, or from a lax ligamentum flavum that collapses into the spinal canal. LSS can present clinical symptoms such as leg pain and reduced function. Conventional treatments include epidural steroid injections, laminotomy, and laminectomy. Surgical interventions which remove at least some portion of the lamina are usually performed through a relatively large incision, and may result in spinal instability from removal of a large portion of the lamina. Consequently, a more percutaneous approach which removes just enough tissue (lamina or ligamentum flavum) to be effective may be beneficial.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ surgical tools such as vertebral rods, inflatable bone tamps and fasteners, for stabilization of a treated section of a spine. There is often little soft tissue and/or bony anatomy to hold the cannula in a stable position during delivery of a surgical tool. To stabilize the cannula, a surgical assistant is often required to provide an extra pair of hands to hold the cannula while a surgeon delivers the tool to the surgical site through the cannula. The present disclosure provides a device that acts as a second pair of hands to hold the cannula at a fixed trajectory to ensure that the cannula is properly positioned relative to the bone defect or bone void.

SUMMARY

Accordingly, a surgical tool holder includes a flange comprising a body defining a first surface and a second surface, a first end and second end. The second surface defines a first opening configured for disposal of a cannula, wherein the first end of the flange is configured to engage at least a portion of skin of a patient to prevent the cannula from moving into the patient.

A surgical tool holder includes a plate comprising a body that defines a first surface and a second surface, a first end and a second end. The plate is configured to engage at least a portion of a posterior spine of a patient. The plate includes an inner surface defining a first opening configured for disposal of a cannula and at least a second inner surface defining at least a second opening configured to receive a K-wire, A surgical tool holder includes a collar comprising a body defining a first surface and a second surface, a first end and a second end, the second surface defines a first opening configured for disposal of a cannula, the first surface defines a second opening in communication with the first opening and configured to receive a locking device, wherein the first end of the flange is configured to engage at least a portion of skin of a patient to prevent the cannula from moving into the patient.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
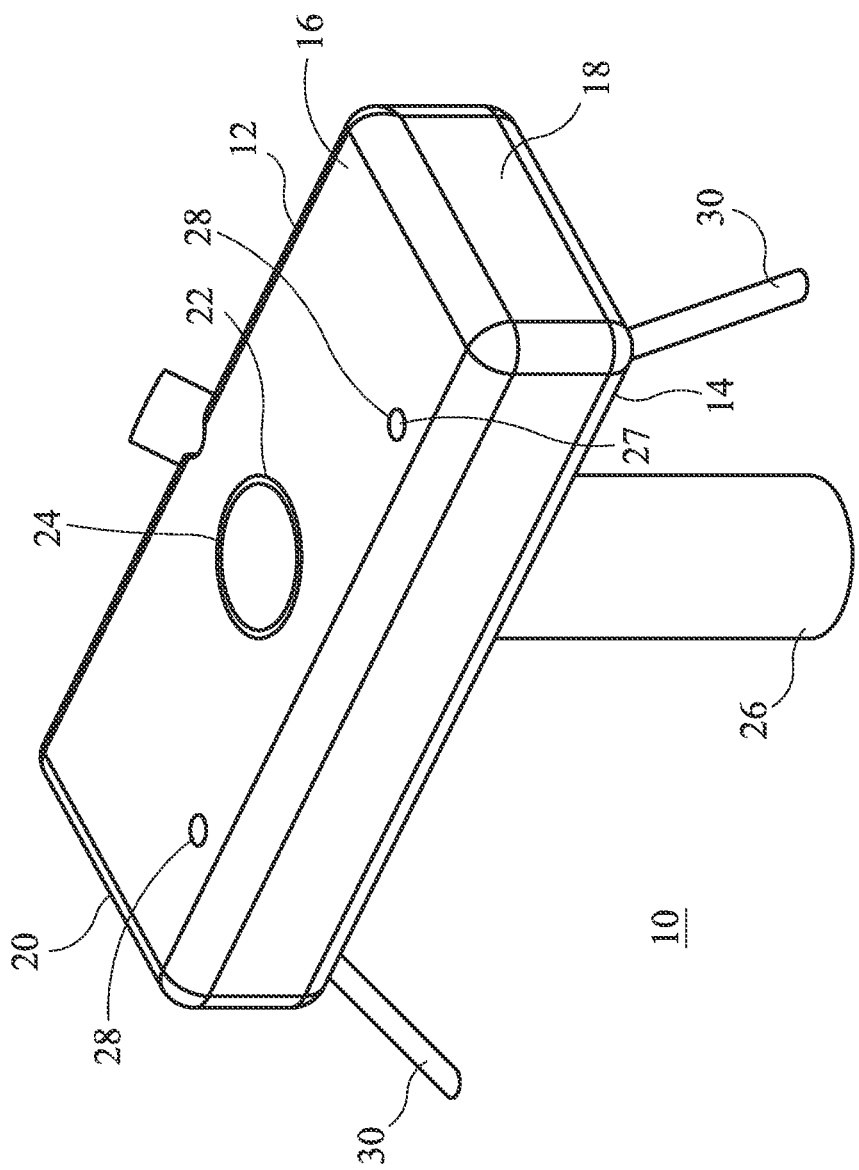
FIG. 1 is a side perspective view of components of one embodiment of a system in accordance with the principles of the present disclosure.

The exemplary embodiments of the surgical tool holder are discussed in terms of medical devices for the treatment of musculoskeletal disorders and more particularly, in terms of a surgical system and method for treatment of a spine disorder. In some embodiments, the surgical tool holder may be employed in applications such as correction of deformities, such as, for example, scoliosis.

In some embodiments, one or all of the components of the spinal implant system may be disposable, peel-pack, pre-packed sterile devices. One or all of the components of the spinal implant system may be reusable. The spinal implant system may be configured as a kit with multiple sized and configured components.

Lumbar spinal stenosis (LSS) may occur from hypertrophied bone or ligamentum flavum, or from a lax ligamentum flavum that collapses into the spinal canal. LSS can present clinical symptoms such as leg pain and reduced function. Conventional treatments include epidural steroid injections, laminotomy, and laminectomy. Surgical interventions which remove at least some portion of the lamina are usually performed through a relatively large incision, and may result in spinal instability from removal of a large portion of the lamina. Consequently, a more percutaneous approach which removes just enough tissue (lamina or ligamentum flavum) to be effective may be beneficial.

In one embodiment, a surgical tool holder is provided that can hold a cannula for percutaneous access to the posterior spine. In one embodiment, a working cannula has a handle. The handle has two holes with pre-determined trajectory to allow passage of K-wires into the spine. The K-wires may be directed to anchor into the lamina, pedicle, facet, or spinous process. In one embodiment, a working cannula passes through a ball joint to allow a variable trajectory. The ball joint may be locked with a thumbscrew.

In one embodiment, a plate includes two oversized holes that allow passage of K-wires into the spine. The K-wires may be directed along a variable trajectory to anchor into the lamina, pedicle, facets, or spinous process. The K-wires are locked into place by advancing a tab against the wires and securing with a thumbscrew. Alternatively, the tabs may have a ratchet feature which mates with the plate. In one embodiment, a working cannula passes through a ball joint to allow a variable trajectory. The ball joint may be locked with a thumbscrew. Two smaller ball joints allow passage of K-wires to anchor into the lamina, pedicle, facets, or spinous process.

The K-wires are locked into place with a thumbscrew. The K-wires may be on the same side of the spine, or may be located on opposite sides.

In some embodiments, the present disclosure may be employed to treat spinal disorders, such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system and method may be employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be employed with procedures for treating the lumbar, cervical, thoracic and pelvic regions of a spinal column. The present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical tool holder, related components and methods for employing the spinal implant system. Alternate embodiments are also disclosed. Reference will now be made in detail to the exemplary embodiments of the present disclosure, which are illustrated in the accompanying figures. Turning now to FIGS. 1-4, there is illustrated components of a surgical tool holder system, such as, for example, a spinal correction device 10 in accordance with the principles of the present disclosure.

The components of device 10 can be fabricated from biologically acceptable materials suitable for medical applications, including metals, synthetic polymers, ceramics and bone material and/or their composites, depending on the particular application and/or preference of a medical practitioner. For example, the components of device 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of device 10 may have material composites, including the above materials, to achieve various desired characteristics such as strength, rigidity, elasticity, compliance, biomechanical performance, durability and radiolucency or imaging preference. The components of device 10, individually or collectively, may also be fabricated from a heterogeneous material such as a combination of two or more of the above-described materials. The components of system 10 may be monolithically formed, integrally connected or include fastening elements and/or instruments, as described herein.

Figure 2:
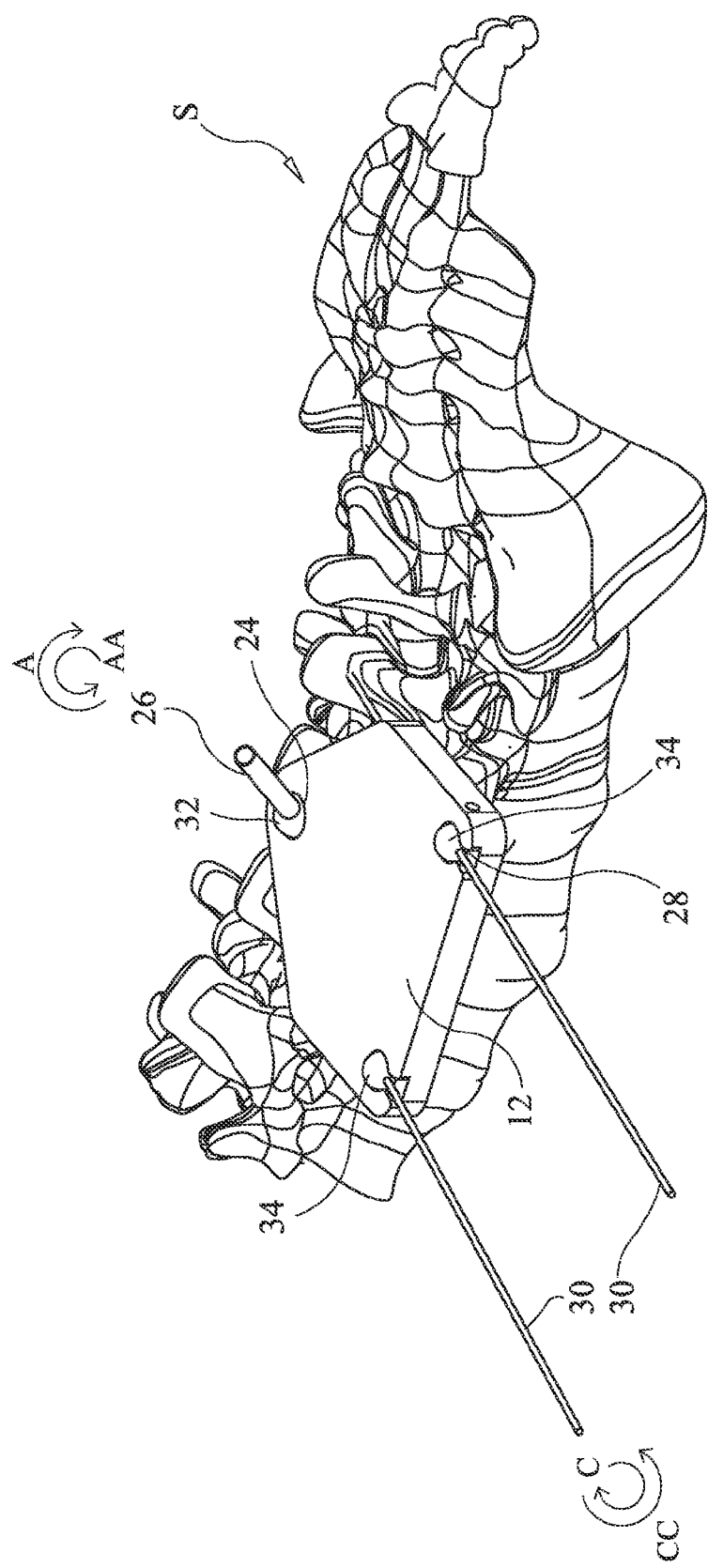
FIG. 2 is a side perspective view of components of one embodiment of a system disposed with vertebrae.
Figure 2A:
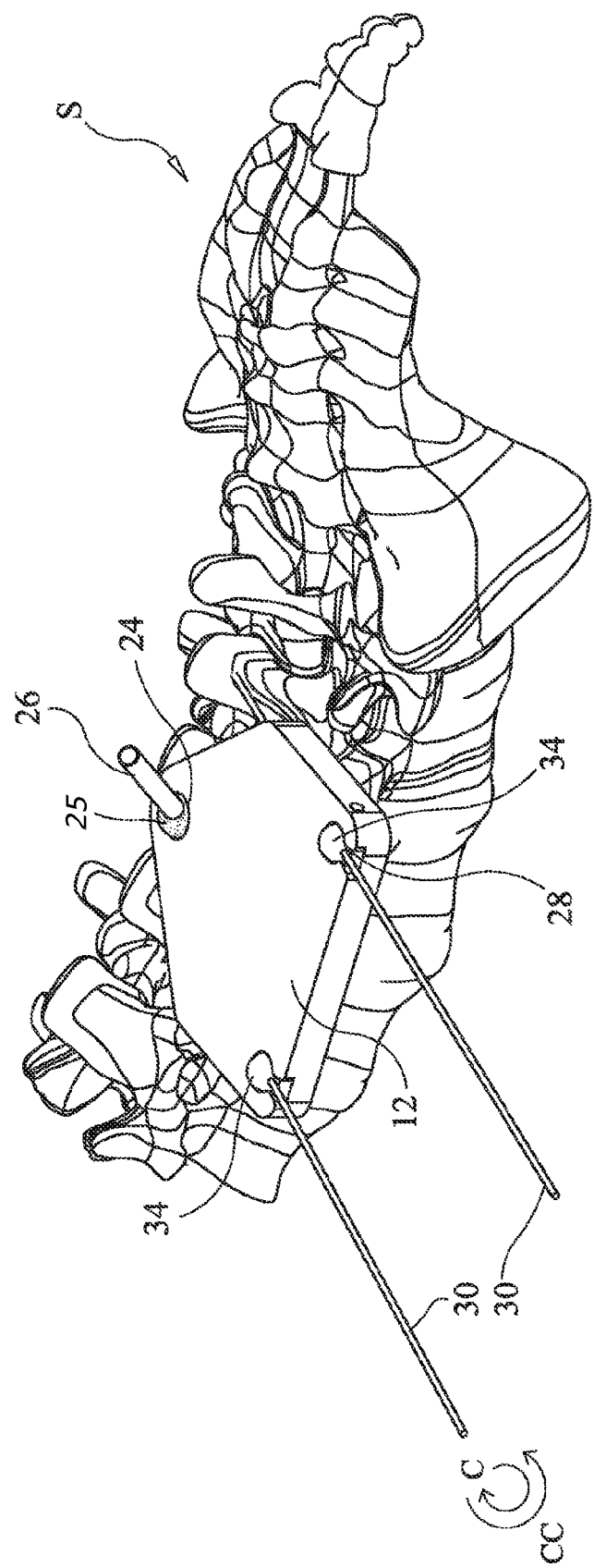
FIG. 2A is a side perspective view of components of one embodiment of a system disposed with a vertebrae.
Figure 3:
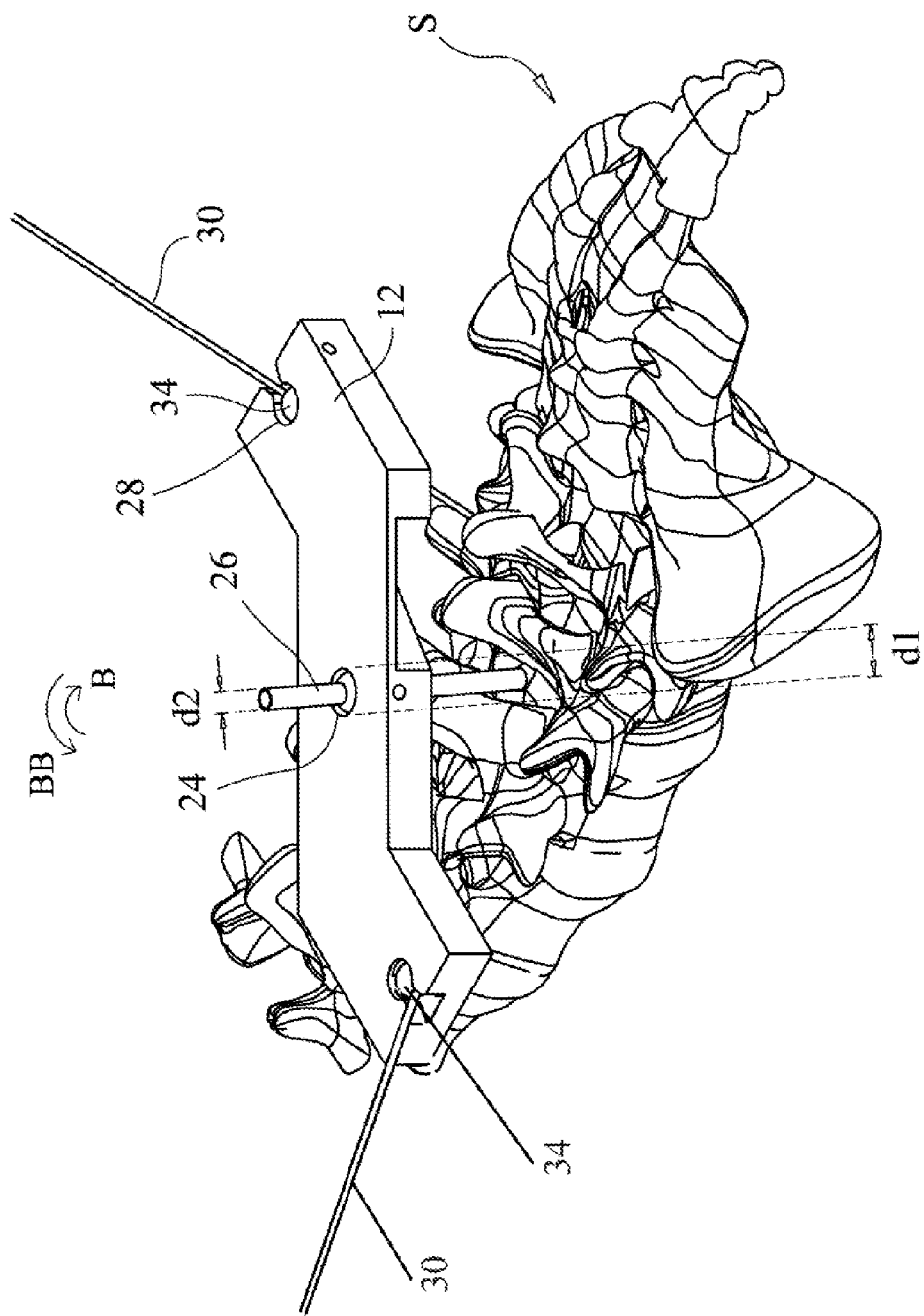
FIG. 3 is a side perspective view of components of one embodiment of a system disposed with vertebrae.
Figure 4:
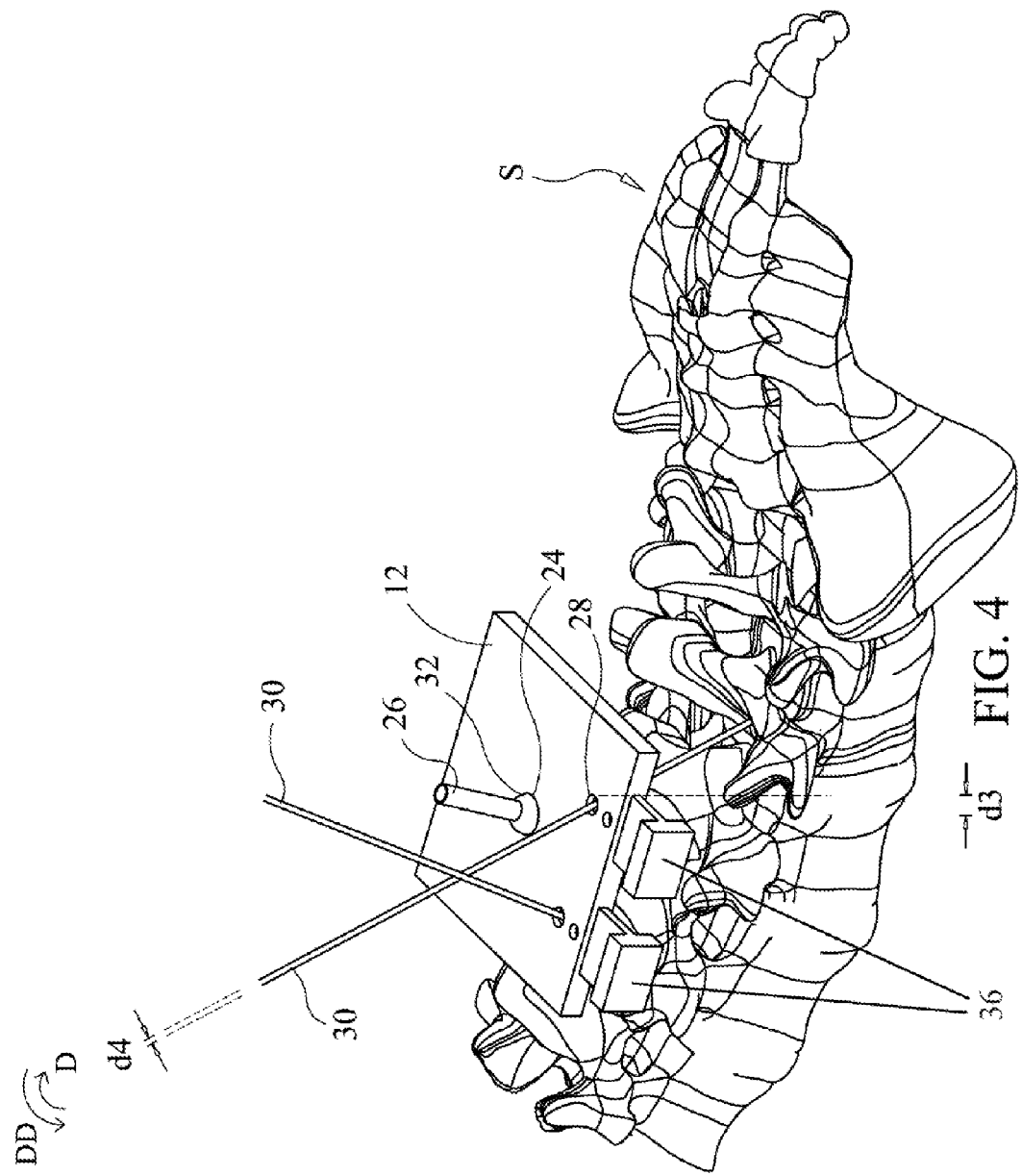
FIG. 4 is a side perspective view of components of one embodiment of a system disposed with vertebrae.

Device 10 includes a surgical tool holder including a flange, such as, for example, a plate 12. Plate 12 has a substantially rectangular configuration. In some embodiments, plate 12 can be variously configured, such as, for example, ergonomically shaped, tubular, oval, oblong, triangular, square, polygonal, irregular, uniform, non-uniform, variable, hollow and/or tapered. Plate 12 includes a first surface 14, second surface 16, a first end 18 and a second end 20. As shown in FIGS. 2-4, plate 12 is configured to engage at least a portion of a posterior spine S on the skin of a patient. In one embodiment, surface 14 may remain a distance from the skin of the patient and not engage the patient. Surface 14 includes substantially planar portions and is oriented in a first direction such that all or only a portion of surface 14 faces and/or engages spine S. Surface 16 is oriented in a second direction, opposite to the first direction. In one embodiment, surface 14 is oriented in a posterior or postero-lateral direction for engagement with the patient's skin. In one embodiment, surface 14 has a frictional surface configuration for engagement with tissue to enhance fixation. In some embodiments, surface 14 may include alternate surface configurations, such as, for example, rough, arcuate, undulating, mesh, porous, semi-porous, dimpled and/or textured according to the requirements of a particular application.

Plate 12 includes an inner surface 22. Surface 22 defines a first opening 24. Opening 24 is configured to receive a surgical tool, such as, for example, a cannula 26. Opening 24 is substantially circular and extends through the thickness of plate 12. In some embodiments, opening 24 can be variously configured, such as, for example, oval, oblong, triangular, square, polygonal, irregular, uniform, non-uniform and/or tapered. In some embodiments, surface 22 may be rough, textured, porous, semi-porous, dimpled and/or polished to facilitate engagement with cannula 26. In one embodiment, plate 12 is configured as a handle disposed with cannula 26 such that cannula 26 and plate 12 are an integrated unit.

Plate 12 includes a second inner surface 27. Surface 27 defines at least a second opening 28. Opening 28 is configured to receive a fixation device, such as, for example, a K-wire 30. Opening 28 is substantially circular and extends through the thickness of plate 12. In some embodiments, opening 28 can be variously configured, such as, for example, oval, oblong, triangular, square, polygonal, irregular, uniform, non-uniform and/or tapered. In some embodiments, surface 27 may be rough, textured, porous, semi-porous, dimpled and/or polished to facilitate engagement with K-wire 30. In some embodiments, other fixation devices may be used, such as, for example, a nail configuration, barbs, expanding elements, raised elements and/or spikes to facilitate engagement of base 12 with the body of the patient. In one embodiment, base 12 includes an adhesive surface or clamping mechanism configured for noninvasive engagement with the body of the patient.

In one embodiment, as shown in FIG. 1, opening 24 includes a fixed trajectory such that cannula 26 extends along the fixed trajectory so as to provide a fixed trajectory for a second surgical tool. In one embodiment, opening 24 includes a deformable insert 25 configured to interact with cannula 26 so as to provide a friction fit with cannula 26. The insert 25 is radially compressible and has a resiliently biased configuration such that the insert 25 collapses to a second orientation and expands to a first orientation. In some embodiments, all or only a portion of the insert 25 may have a semi-rigid, rigid or elastic configuration, and/or have elastic properties, such as the elastic properties corresponding to the material examples described above, such that the insert 25 provides a selective amount of expansion, contraction, collapse and/or extension. In some embodiments, the insert 25 may be compressible in an axial direction. The insert 25 can include a plurality of separately attachable or connectable portions or sections, such as bands or loops, or may be monolithically formed as a single continuous element.

In one embodiment, as shown in FIGS. 2 and 4, opening 24 includes a rotational element, such as, for example, a ball socket 32. Ball socket 32 is configured to provide for a variable trajectory of cannula 26 through plate 12 and into the patient. As cannula 26 slides through socket 32, cannula 26 can be rotated and angled as shown by arrows A and AA with respect to plate 12 to a desired trajectory and then cannula 26 can be locked in place, as discussed below. The cannula can also translate along its axis in addition to rotating.

In one embodiment, as shown in FIG. 3, opening 24 includes a diameter d1 larger than a diameter d2 of cannula 26. The difference in diameter allows cannula 26 to be moveable with a variable trajectory through the plate and into the patient. As cannula 26 slides through larger diameter opening 24, cannula 26 can be rotated and angled as shown by arrows B and BB with respect to plate 12 to a desired trajectory. The larger diameter opening allows for cannula 26 to be rotated within opening 24 and then locked in place, as discussed below.

In one embodiment, as shown in FIG. 1, opening 28 defines a fixed trajectory for K-wire 30 through plate 12 and into the patient. In one embodiment, as shown in FIGS. 2-3, opening 28 includes a rotational element, such as, for example, a ball socket 34. Ball socket 34 is configured to provide for a variable trajectory of K-wire 30 through plate 12 and into the patient. As K-wire 30 slides through socket 34, K-wire 30 can be rotated and angled as shown by arrows C and CC with respect to plate 12 to a desired trajectory.

In one embodiment, as shown in FIG. 4, opening 28 includes a diameter d3 larger than a diameter d4 of K-wire 30. The difference in diameter allows K-wire 30 to be moveable in a variable trajectory through the plate and into the patient. As K-wire 30 slides through larger diameter opening 24, K-wire 30 can be rotated and angled as shown by arrows D and DD with respect to plate 12 to a desired trajectory.

In one embodiment, opening 24 includes a locking device, such as, for example, a set screw or a thumb screw, not shown. The locking device locks cannula 26 in a particular trajectory as needed for a particular procedure. In one embodiment, opening 28 includes a locking device, such as, for example, a locking tab 36 and/or a thumb screw (not shown) to lock K-wire 30 in a particular trajectory. Tab 36 may include a ratchet feature such that allows for incremental movement of tab 36 to lock K-wire 30 in place. Once K-wire 30 is positioned in the desired fixed trajectory, tab 36 is slid into place to lock K-wire 30 in place.

In operation, assembly and use, device 10 is employed with a surgical procedure for treatment of a bone disorder, such as, for example, decompression of spinal stenosis. Plate 12 is placed over the spine S of the patient. Plate 12 is manipulated and positioned such that openings 26 and 28 are placed in a desired location according to the particular procedure. K-wires 30 are positioned within through openings 28 and are disposed in the anatomy of the patient, such as, for example, the pedicle bone, to fix or stabilize device 10 relative to the anatomy of the patient. Once device 10 is stabilized, cannula 26 is positioned within opening 24 such that a distal end of cannula 26 is positioned adjacent the bone disorder and cannula 26 is moveable to the desired trajectory and is then locked in place. In one embodiment, cannula 26 is positioned within through openings 24 and then K-wires 30 are positioned within through openings 28 and are disposed in the anatomy of the patient, such as, for example, the pedicle to stabilize the device. A surgical tool may be delivered through cannula 26 to a location adjacent the bone disorder or defect.

Device 10 maintains cannula 26 in a stabilized orientation with respect to the body such that a fixed trajectory to the surgical site is maintained.

Figure 5:
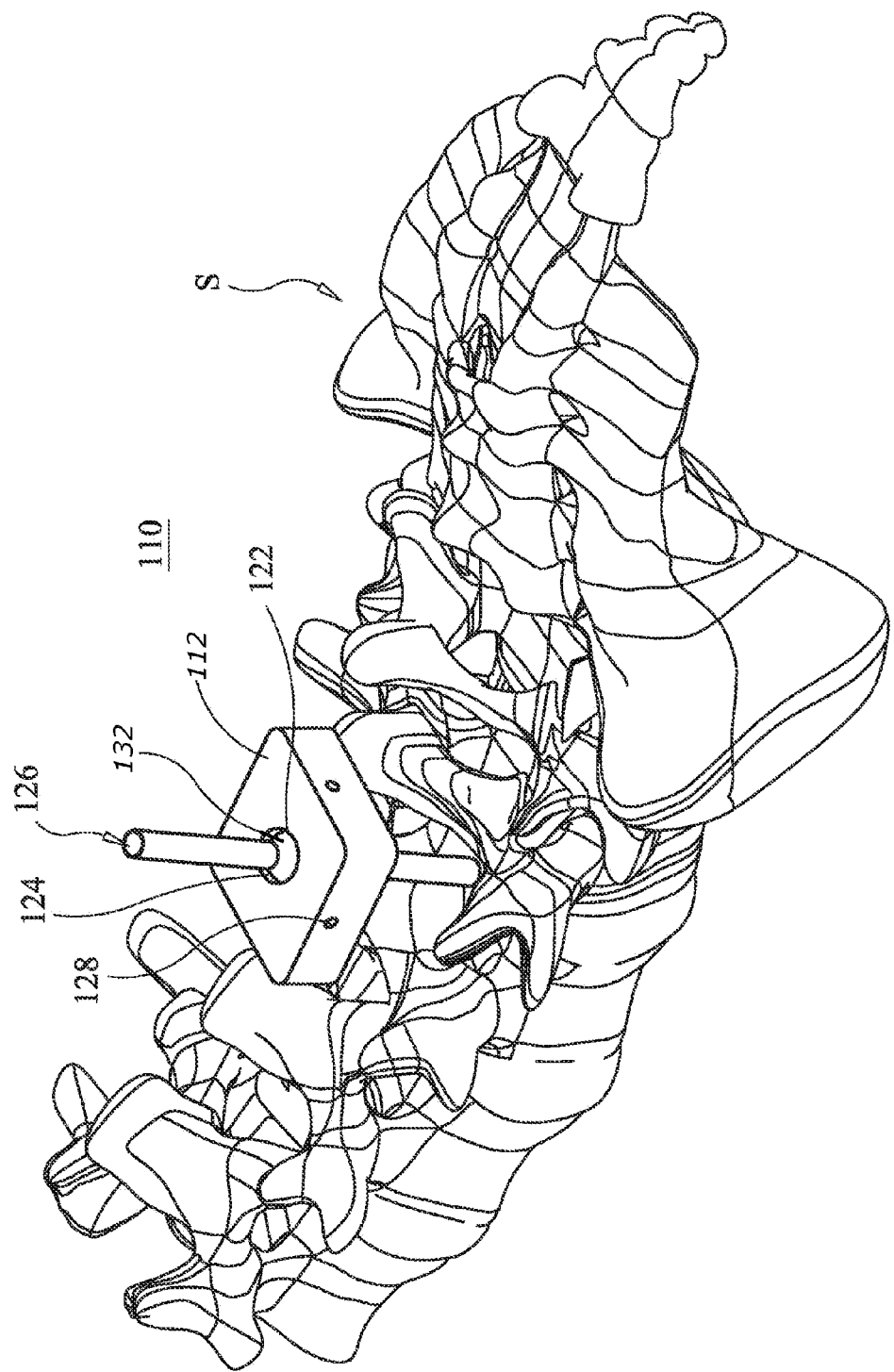
FIG. 5 is a side perspective view of components of one embodiment of a system in accordance with the principles of the present disclosure.

In one embodiment, as shown in FIG. 5, device 110 includes a surgical tool holder including a plate 112. Plate 112 has a substantially square configuration. In some embodiments, plate 112 can be variously configured, such as, for example, ergonomically shaped, tubular, oval, oblong, triangular, rectangular, polygonal, irregular, uniform, non-uniform, variable, hollow and/or tapered. Plate 112 includes an inner surface 122. Surface 122 defines a first opening 124. Opening 124 is configured to receive a surgical tool, such as, for example, a cannula 126. Opening 124 is substantially circular and extends through the thickness of plate 112. Opening 124 includes a rotational element, such as, for example, a ball socket 132. Opening 124 mates with ball socket 132. Ball socket 132 is configured to provide for a variable trajectory of cannula 126 through plate 112 and into the patient. In one embodiment, at least a second opening 128 is disposed in plate 112. Opening 128 is in communication with opening 124 such that a locking device, such as, for example, a set screw or a thumb screw (not shown) can be inserted into opening 128 to lock cannula 126 in place within opening 124. The locking device locks cannula 126 in a particular trajectory as needed for a particular procedure.

Figure 6:
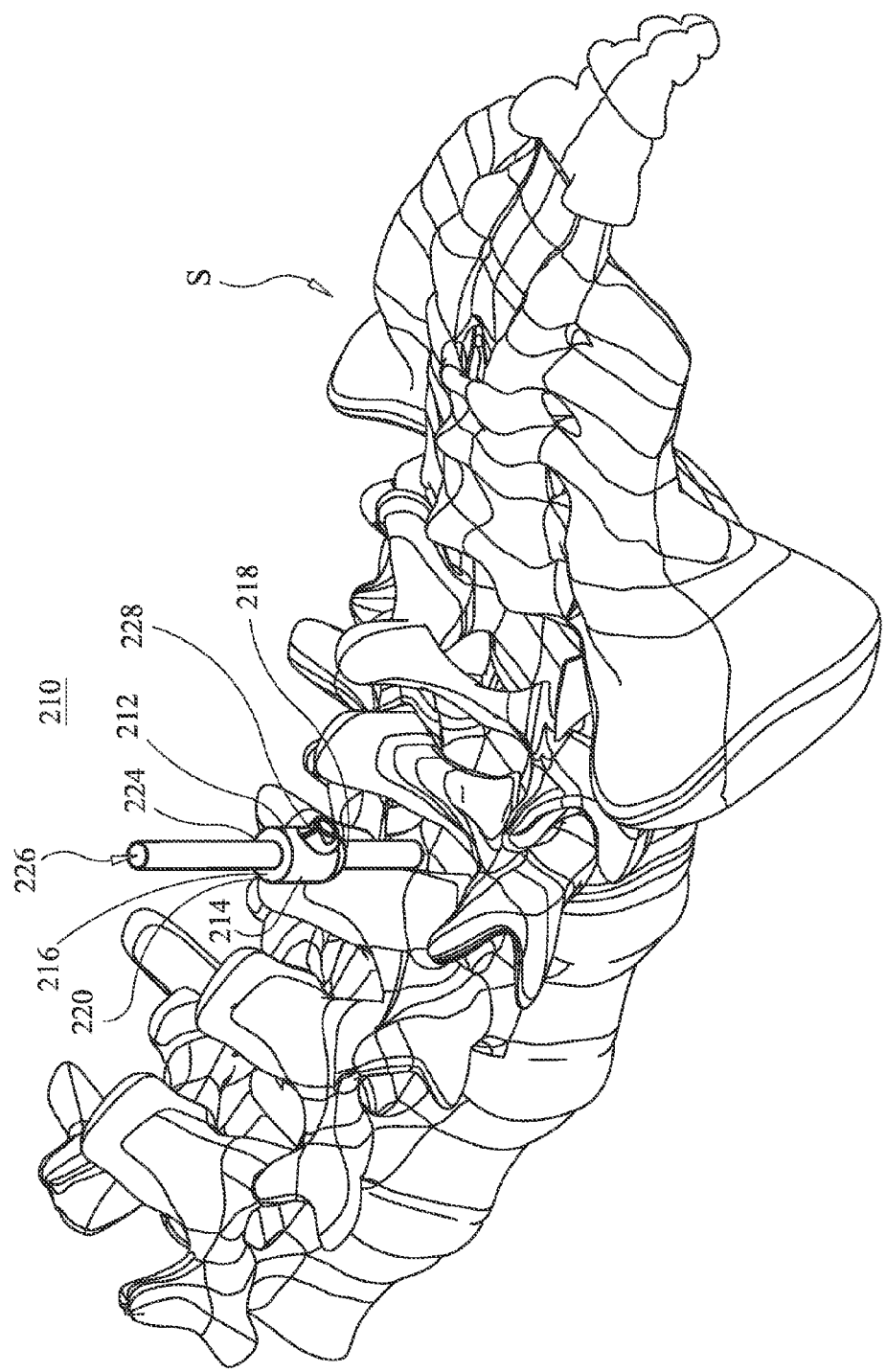
FIG. 6 is a side perspective view of components of one embodiment of a system in accordance with the principles of the present disclosure.

In one embodiment, as shown in FIG. 6, device 210 includes a surgical tool holder including a collar 212. Collar 212 includes a first surface 214, second surface 216, a first end 218 and a second end 220. Collar 212 has a substantially cylindrical configuration. In some embodiments, collar 212 can be variously configured, such as, for example, ergonomically shaped, tubular, oval, oblong, triangular, rectangular, polygonal, irregular, uniform, non-uniform, variable, hollow and/or tapered. Surface 216 defines a first opening 224. Opening 224 is configured to receive a surgical tool, such as, for example, a cannula 226. Opening 224 is substantially circular and extends through the thickness of collar 212. In one embodiment, at least a second opening 228 is disposed in collar 212. Opening 228 is in communication with opening 224 such that a locking device, such as, for example, a set screw or a thumb screw (not shown) can be inserted into opening 228 to lock cannula 226 in place within opening 224. The locking device locks cannula 226 in a particular trajectory as needed for a particular procedure. End 218 is configured to rest on the skin a patient thereby preventing cannula 226 from moving deeper into the body of the patient once locked in place in collar 212.

In some embodiments, the agent may include therapeutic polynucleotides or polypeptides. In some embodiments, the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of system 10 can be made of radiolucent materials such as polymers. Radiomarkers may be included for identification under x-ray, fluoroscopy, CT or other imaging techniques.

In some embodiments, the use of microsurgical and image guided technologies may be employed to access, view and repair spinal deterioration or damage, with the aid of system 10. Upon completion of the procedure, the surgical instruments, assemblies and non-implant components of system 10 are removed from the surgical site and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical tool holder comprising:
    a plate comprising a body defining a first end surface and an opposite second end surface, the first and second end surfaces each extending between opposite first and second side surfaces, the body comprising opposite top and bottom surfaces that each extend between the first and second end surfaces and between the first and second side surfaces, the plate configured to engage at least a portion of skin of a patient, the plate including a first opening extending through the top and bottom surfaces configured for disposal of a cannula and a second opening extending through the top and bottom surfaces that is spaced apart from the first opening and configured to receive a fixation device, the plate comprising a channel extending through the top surface and the second end surface without extending through the bottom surface or the first end surface, the channel being in communication with the second opening and configured to receive the fixation device when the fixation device extends transverse to the second opening; and
    further comprising the fixation device, wherein the fixation device is a K-wire.

2. A surgical tool holder as recited in claim 1, wherein the first opening has a diameter that is larger than a diameter of the cannula so that the cannula is moveable in a variable trajectory relative to the body when the cannula is positioned within the first opening.

3. A surgical tool holder as recited in claim 1, wherein the first opening includes a ball joint rotatably disposed therein, the cannula extending through the ball joint such that the cannula is rotatable relative to the body to provide the cannula with a variable trajectory relative to the plate.

4. A surgical tool holder according to claim 1, further comprising:
    a locking device, the locking device being configured to engage.

5. A surgical tool holder as recited in claim 4, wherein the locking device is a set screw.

6. A surgical tool holder as recited in claim 4, wherein the body comprises a collar, the collar having a cylindrical configuration.

7. A surgical tool holder comprising:
    a plate comprising a body defining a first end surface and an opposite second end surface, the first and second end surfaces each extending between opposite first and second side surfaces, the body comprising opposite top and bottom surfaces that each extend between the first and second end surfaces and between the first and second side surfaces, the plate configured to engage at least a portion of skin of a patient, the plate including a first opening extending through the top and bottom surfaces configured for disposal of a cannula and a second opening extending through the top and bottom surfaces that is spaced apart from the first opening and configured to receive a fixation device, the plate comprising a channel extending through the top surface and the second end surface without extending through the bottom surface or the first end surface, the channel being in communication with the second opening and configured to receive the fixation device when the fixation device extends transverse to the second opening; and the fixation device, wherein the fixation device comprises a first K-wire that is positioned in the second opening and a second K-wire; and wherein the plate comprises a third opening extending through the top and bottom surfaces that is spaced apart from the first opening and the second opening, the third opening having the second K-wire positioned therein, the plate comprising a second channel extending through the top surface and the second end surface without extending through the bottom surface or the first end surface, the second channel being in communication with the third opening and configured to receive a portion of the second K-wire device when the second K-wire extends transverse to the top surface.

8. A surgical tool holder as recited in claim 7, wherein the second opening includes a ball joint that is rotatable relative to the body, the fixation device being positioned within the ball joint to provide the fixation device with a variable trajectory relative to the plate.

9. A surgical tool holder as recited in claim 7, wherein the first opening includes a diameter that is larger than a diameter of the cannula to provide for a variable trajectory for the cannula relative to the plate when the cannula is positioned within the first opening.

10. A surgical tool holder comprising:

a plate comprising a body defining a first end surface and an opposite second end surface, the first and second end surfaces each extending between opposite first and second side surfaces, the body comprising opposite top and bottom surfaces that each extend between the first and second end surfaces and between the first and second side surfaces, the plate configured to engage at least a portion of skin of a patient, the plate including a first opening extending through the top and bottom surfaces configured for disposal of a cannula and a second opening extending through the top and bottom surfaces that is spaced apart from the first opening and configured to receive a fixation device, the plate comprising a channel extending through the top surface and the second end surface without extending through the bottom surface or the first end surface, the channel being in communication with the second opening and configured to receive the fixation device when the fixation device extends transverse to the second opening; and the fixation device, wherein the fixation device comprises a first K-wire that is positioned in the second opening and a second K-wire; and wherein the plate comprises a third opening extending through the top and bottom surfaces that is spaced apart from the first opening and the second opening, the third opening having the second K-wire positioned therein, the plate comprising a second channel extending through the top surface and the first end surface without extending through the bottom surface or the second end surface, the second channel being in communication with the third opening and configured to receive a portion of the second K-wire device when the second K-wire extends transverse to the top surface.

* * * * *